(12) United States Patent
Pien et al.

(10) Patent No.: US 7,217,574 B2
(45) Date of Patent: May 15, 2007

(54) METHOD AND APPARATUS FOR BIOSENSOR SPECTRAL SHIFT DETECTION

(75) Inventors: Homer Pien, Andover, MA (US); William C. Karl, North Andover, MA (US); Derek Puff, Long Beach, CA (US); Peter Li, Andover, MA (US); Brian Cunningham, Lexington, MA (US)

(73) Assignee: SRU Biosystems, Inc., Woburn, MA (US)

( * ) Notice: Subject to any disclaimer, the term of this patent is extended or adjusted under 35 U.S.C. 154(b) by 687 days.

(21) Appl. No.: 10/253,846

(22) Filed: Sep. 25, 2002

(65) Prior Publication Data

US 2003/0077660 A1 Apr. 24, 2003

Related U.S. Application Data

(63) Continuation-in-part of application No. 10/059,060, filed on Jan. 28, 2002, now Pat. No. 7,070,987, and a continuation-in-part of application No. 10/058,626, filed on Jan. 28, 2002, now Pat. No. 6,951,715, which is a continuation-in-part of application No. 09/930,352, filed on Aug. 15, 2001, now Pat. No. 7,094,595.

(60) Provisional application No. 60/303,028, filed on Jul. 3, 2001, provisional application No. 60/283,314, filed on Apr. 12, 2001, provisional application No. 60/244,312, filed on Oct. 30, 2000.

(51) Int. Cl.
  *G01N 21/00* (2006.01)
(52) U.S. Cl. ............... 436/164; 436/516; 436/805
(58) Field of Classification Search .............. None
  See application file for complete search history.

(56) References Cited

U.S. PATENT DOCUMENTS 3,689,346 A 9/1972 Rowland ............... 156/245

(Continued)

FOREIGN PATENT DOCUMENTS

CA 2394966 2/2001

(Continued)

OTHER PUBLICATIONS

Liu, et al., "Development of an optical fiber lactate sensor", Mikrochimica Acta, 1999, 131(1-2), pp. 129-135.

(Continued)

*Primary Examiner*—Christopher L. Chin
(74) *Attorney, Agent, or Firm*—McDonnell Boehnen Hulbert & Berghoff LLP

(57) ABSTRACT

Performing high-resolution determination of the relative shift of the spectral properties of a biosensor. The shift in the resonance peak of the biosensor is indicative of the amount of material bound to the surface of the biosensor. A preferred biosensor is a Guided Mode Resonant Filter Biosensor (GMRFB). In one aspect of the invention, curve fitting is used to determine the relative location of the spectrum of the unexposed biosensor with respect to those spectra that are altered (e.g., shifted) by the presence of materials bound to the surface of the biosensor. In an alternative embodiment, the cross correlation function is used to detect spectral peak offsets between a reference spectrum and a spectrum measured from an exposed biosensor. In yet another alternative, maximal likelihood estimation techniques are used to determine the spectral shift or offs.

14 Claims, 7 Drawing Sheets

U.S. PATENT DOCUMENTS

| | | | | |
|---|---|---|---|---|
| 3,810,688 | A | 5/1974 | Ballman et al. | 350/96 |
| 3,856,404 | A | 12/1974 | Hershler et al. | 156/361 |
| 3,856,604 | A | 12/1974 | Hershler et al. | 156/361 |
| 4,009,933 | A | 3/1977 | Firester | |
| 4,050,895 | A | 9/1977 | Hardy et al. | 436/527 |
| 4,240,751 | A | 12/1980 | Linnecke et al. | 356/409 |
| 4,289,371 | A | 9/1981 | Kramer | 350/3.71 |
| 4,344,438 | A | 8/1982 | Schultz | 128/633 |
| 4,420,502 | A | 12/1983 | Conley | 427/54.1 |
| 4,536,608 | A | 8/1985 | Sheng et al. | |
| 4,560,248 | A | 12/1985 | Cramp et al. | 385/12 |
| 4,576,850 | A | 3/1986 | Martens | |
| 4,608,344 | A | 8/1986 | Carter et al. | 436/34 |
| 4,650,329 | A | 3/1987 | Barrett et al. | 356/481 |
| 4,652,290 | A | 3/1987 | Cho et al. | 65/31 |
| 4,668,558 | A | 5/1987 | Barber | |
| 4,701,008 | A | 10/1987 | Richard et al. | 385/132 |
| 4,810,658 | A | 3/1989 | Shanks et al. | 436/172 |
| 4,815,843 | A | 3/1989 | Tiefenthaler et al. | 356/128 |
| 4,818,710 | A | 4/1989 | Sutherland et al. | 436/527 |
| 4,857,273 | A | 8/1989 | Stewart et al. | 436/82 |
| RE33,064 | E | 9/1989 | Carter | 436/34 |
| 4,876,208 | A | 10/1989 | Gustafson et al. | |
| 4,882,288 | A | 11/1989 | North et al. | 436/525 |
| 4,888,260 | A | 12/1989 | Cowan | 403/1 |
| 4,931,384 | A | 6/1990 | Layton et al. | 435/7 |
| 4,952,056 | A | 8/1990 | Tiefenthaler | 356/73.1 |
| 4,958,895 | A | 9/1990 | Wells et al. | 350/96.12 |
| 4,992,385 | A | 2/1991 | Godfrey | 436/525 |
| 4,999,234 | A | 3/1991 | Cowen | 428/156 |
| 5,071,248 | A | 12/1991 | Tiefenthaler et al. | 356/128 |
| 5,118,608 | A | 6/1992 | Layton et al. | 435/7.1 |
| 5,155,785 | A | 10/1992 | Holland et al. | 385/89 |
| 5,156,785 | A | 10/1992 | Zdrahala | 264/334 |
| 5,170,448 | A | 12/1992 | Ackley et al. | 385/31 |
| 5,175,030 | A | 12/1992 | Lu et al. | 428/30 |
| 5,210,404 | A | 5/1993 | Cush et al. | 250/216 |
| 5,229,614 | A | 7/1993 | Anderson et al. | 250/370.12 |
| 5,242,828 | A | 9/1993 | Bergströet al. | 435/291 |
| 5,268,782 | A | 12/1993 | Wenz et al. | 359/81 |
| 5,310,686 | A | 5/1994 | Sawyers et al. | |
| 5,337,183 | A | 8/1994 | Rosenblatt | 359/248 |
| 5,413,884 | A | 5/1995 | Koch et al. | 430/5 |
| 5,442,169 | A | 8/1995 | Kunz | 250/227.21 |
| 5,455,178 | A | 10/1995 | Fattinger | 436/164 |
| 5,475,780 | A | 12/1995 | Mizrahi | 385/37 |
| 5,478,527 | A | 12/1995 | Gustafson et al. | 422/82 |
| 5,478,756 | A | 12/1995 | Gizeli et al. | 436/527 |
| 5,492,840 | A | 2/1996 | Malmquist et al. | |
| 5,496,701 | A | 3/1996 | Pollard-Knight | 435/7.4 |
| 5,559,338 | A | 9/1996 | Elliott et al. | 250/492.1 |
| 5,598,267 | A | 1/1997 | Sambles et al. | 356/369 |
| 5,598,300 | A | 1/1997 | Magnusson et al. | 359/566 |
| 5,606,170 | A | 2/1997 | Saaski et al. | 250/458.1 |
| 5,615,052 | A | 3/1997 | Doggett | 359/811 |
| 5,629,214 | A | 5/1997 | Crosby | 436/518 |
| 5,631,171 | A | 5/1997 | Sandstrom et al. | 436/518 |
| 5,690,894 | A | 11/1997 | Pinkel et al. | 422/68.1 |
| 5,691,846 | A | 11/1997 | Benson et al. | 359/530 |
| 5,732,173 | A | 3/1998 | Bylander et al. | 385/49 |
| 5,738,825 | A | 4/1998 | Rudigier et al. | 422/82 |
| 5,768,461 | A | 6/1998 | Svetkoff et al. | 385/116 |
| 5,771,328 | A | 6/1998 | Wortman et al. | 385/146 |
| 5,792,411 | A | 8/1998 | Morris et al. | 264/400 |
| 5,801,390 | A | 9/1998 | Shiraishi | 250/559.3 |
| 5,804,453 | A | 9/1998 | Chen | |
| 5,814,524 | A | 9/1998 | Walt et al. | 436/514 |
| 5,821,343 | A | 10/1998 | Keogh | |
| 5,846,843 | A | 12/1998 | Simon | |
| 5,864,641 | A | 1/1999 | Murphy et al. | 385/12 |
| 5,922,550 | A | 7/1999 | Everhart et al. | 435/7.21 |
| 5,925,878 | A | 7/1999 | Challener | |
| 5,955,335 | A | 9/1999 | Thust et al. | |
| 5,955,378 | A | 9/1999 | Challener | |
| 5,986,762 | A | 11/1999 | Challener | |
| 5,991,480 | A | 11/1999 | Kunz et al. | |
| 5,994,150 | A | 11/1999 | Challener et al. | |
| 5,998,298 | A | 12/1999 | Hetherington et al. | |
| 6,035,089 | A | 3/2000 | Grann et al. | |
| 6,042,998 | A | 3/2000 | Brueck et al. | |
| 6,052,213 | A | 4/2000 | Burt et al. | 359/237 |
| 6,076,248 | A | 6/2000 | Hoopman et al. | |
| 6,088,505 | A | 7/2000 | Hobbs | |
| 6,100,991 | A | 8/2000 | Challener | |
| 6,128,431 | A | 10/2000 | Siminovitch | 385/147 |
| 6,146,593 | A | 11/2000 | Pinkel et al. | |
| 6,174,677 | B1 | 1/2001 | Vo-Dinh | 356/301 |
| 6,185,019 | B1 | 2/2001 | Hobbs et al. | 359/30 |
| 6,200,737 | B1 | 3/2001 | Walt et al. | 430/320 |
| 6,215,928 | B1 | 4/2001 | Friesem et al. | 385/37 |
| 6,218,194 | B1 | 4/2001 | Lyndin et al. | 436/518 |
| 6,235,488 | B1 | 5/2001 | Tom-Moy et al. | |
| 6,303,179 | B1 | 10/2001 | Koulik et al. | |
| 6,316,153 | B1 | 11/2001 | Goodman et al. | 430/8 |
| 6,320,991 | B1 | 11/2001 | Challener et al. | |
| RE37,473 | E | 12/2001 | Challener | |
| 6,338,968 | B1 | 1/2002 | Hefti | |
| 6,340,598 | B1 | 1/2002 | Herron et al. | |
| 6,346,376 | B1 | 2/2002 | Sigrist et al. | |
| 6,377,721 | B1 | 4/2002 | Walt et al. | 385/12 |
| 6,404,554 | B1 | 6/2002 | Lee et al. | 359/576 |
| 6,449,097 | B1 | 9/2002 | Zhu et al. | 359/576 |
| 6,558,957 | B1 | 5/2003 | Roinestad et al. | 422/82.05 |
| 6,570,657 | B1 | 5/2003 | Hoppe et al. | 356/445 |
| 6,579,673 | B2 | 6/2003 | McGrath et al. | 435/5 |
| 6,587,276 | B2 | 7/2003 | Daniell | 359/622 |
| 6,661,952 | B2 | 12/2003 | Simpson et al. | 385/37 |
| 6,707,561 | B1 | 3/2004 | Budach et al. | 356/521 |
| 6,748,138 | B2 | 6/2004 | Wang et al. | 385/37 |
| 6,902,703 | B2 | 6/2005 | Marquiss et al. | |
| 2002/0018610 | A1 | 2/2002 | Challener et al. | |
| 2002/0123050 | A1 | 9/2002 | Poponin | 356/301 |
| 2002/0127565 | A1 | 9/2002 | Cunningham et al. | |
| 2002/0135752 | A1 | 9/2002 | Sokolov et al. | 356/39 |
| 2002/0168295 | A1 | 11/2002 | Cunningham et al. | |
| 2002/0171045 | A1 | 11/2002 | Perraut | |
| 2003/0003599 | A1 | 1/2003 | Wagner et al. | |
| 2003/0017580 | A1 | 1/2003 | Cunningham et al. | |
| 2003/0017581 | A1 | 1/2003 | Li et al. | |
| 2003/0026891 | A1 | 2/2003 | Qiu et al. | |
| 2003/0027327 | A1 | 2/2003 | Cunningham et al. | |
| 2003/0027328 | A1 | 2/2003 | Cunningham et al. | |
| 2003/0032039 | A1 | 2/2003 | Cunningham et al. | |
| 2003/0059855 | A1 | 3/2003 | Cunningham et al. | |
| 2003/0068657 | A1 | 4/2003 | Lin et al. | |
| 2003/0077660 | A1 | 4/2003 | Pien et al. | |
| 2003/0092075 | A1 | 5/2003 | Pepper | |
| 2003/0113766 | A1 | 6/2003 | Pepper et al. | |
| 2003/0148542 | A1 | 8/2003 | Pawlak | |
| 2003/0210396 | A1 | 11/2003 | Hobbs et al. | 356/416 |
| 2004/0011965 | A1 | 1/2004 | Hodgkinson | 356/317 |
| 2004/0132172 | A1 | 7/2004 | Cunningham et al. | |
| 2004/0132214 | A1 | 7/2004 | Lin et al. | |
| 2004/0151626 | A1 | 8/2004 | Cunningham et al. | |

FOREIGN PATENT DOCUMENTS

| | | |
|---|---|---|
| CA | 2395318 | 2/2001 |
| CA | 2394966 | 8/2001 |
| CA | 2395318 | 8/2001 |
| CH | 669050 A5 | 2/1989 |
| CH | 670521 A5 | 6/1989 |
| EP | 0326219 | 1/1989 |
| EP | 0326291 | 2/1989 |

| | | |
|---|---|---|
| EP | 0 660 924 | 9/1999 |
| FR | 2801977 | 2/1999 |
| FR | 2801977 | 12/1999 |
| GB | 2156970 A | 10/1985 |
| GB | 2 227 089 | 7/1990 |
| WO | WO 81/00912 | 2/1981 |
| WO | 8100912 | 4/1981 |
| WO | 0075353 | 3/1983 |
| WO | WO 84/02578 | 7/1984 |
| WO | 8607149 | 12/1986 |
| WO | WO 90/08313 | 7/1990 |
| WO | WO 91/13339 | 9/1991 |
| WO | WO 92/04653 | 3/1992 |
| WO | WO 92/21768 | 12/1992 |
| WO | WO 93/14392 | 7/1993 |
| WO | WO 95/03538 | 2/1995 |
| WO | WO 98/57200 | 12/1998 |
| WO | WO 99/09392 | 2/1999 |
| WO | WO 99/09396 | 2/1999 |
| WO | 9954714 | 10/1999 |
| WO | WO 99/66330 | 12/1999 |
| WO | WO 00/23793 | 4/2000 |
| WO | 0029830 | 5/2000 |
| WO | WO 01/04697 | 1/2001 |
| WO | WO 02/061429 | 8/2002 |

OTHER PUBLICATIONS

*Coming Inc. v. SRU Biosystems, Inc.*, Memorandum Opinion dated Nov. 15, 2005 in the United States District Court for the district of Delaware.
U.S. Appl. No. 60/244,312, filed Oct. 30, 2000, Cunningham, et al.
U.S. Appl. No. 60/283,314, filed Apr. 12, 2001, Cunningham, et al.
U.S. Appl. No. 60/303,028, filed Jul. 3, 2001, Cunningham, et al.
Brecht, et al., "Optical probes and transducers", *Biosensors & Bioelectronics* vol. 10, pp. 923-936 (1995).
Challener, et al., "A multilayer grating-based evanescent wave sensing technique", *Sensors and Actuators B*, 71, pp. 42-46 (2000).
Cowan, "Aztec surface-relief volume diffractive structure", *J. Opt. Soc. Am.*, vol. 7, No. 8, pp. 1529-1544 (1990).
Cowan, "Holographic honeycomb microlens", *Optical Engineering*, vol. 24, No. 5, pp. 796-802 (1985).
Cowan, "The Recording and Large Scale Replication of Crossed Holographic Grating Arrays using Multiple Beam Interferometry", *SPIE* vol. 503, Application, Theory, and Fabrication of Periodic Structures, pp. 120-129 (1984).
Cowan, et al., "The Recording and Replication of Holographic Micropatterns for the Ordering of Photographic Emulsion Grains in Film Systems", *J. Imaging Sci.*, vol. 31, No. 3, pp. 100-107 (1987).
Cunningham, B. et al., "A plastic colorimetric resonant optical biosensor for multiparallel detection of label-free biochemical interactions", *Sensors and Actuators B* 85; pp. 219-226 (2002).
Cunningham, B. et al., "Colorimetric resonant reflection as a direct biochemical assay technique", *Sensors and Actuators B* 81; pp. 316-328 (2002).
Cunningham, "Optically Based Energy Transduction", *Techniques in Analytical Chemistry*, pp. 260-291.
Hobbs, et al., "Automated Interference Lithography Systems for Generation of Sub-Micron Feature Size Patterns", *SPIE*, vol. 3879, pp. 124-135, (1999).
Huber, et al., "Direct optical immunosensing sensitivity and selectivity)", *Sensors and Actuators B*, 6, pp. 122-126 (1992).
Jenison, et al., "Interference-based detection of nucleic acid targets on optically coated silicon", *Nature Biotechnology*, vol. 19, pp. 62-64 (2001).
Jin, et al., " A biosensor concept based on imaging ellipsometry for visualization of biomolecular interactions", *Analytical Biochemistry*, vol. 232, pp. 69-72 (1995).
Jordan, et al., "Surface Plasmon Resonance Imaging Measurements of Electrostatic Biopolymer Adsorption onto Chemically Modified Gold Surfaces", *Analytical Chemistry*, vol. 69, No. 7, pp. 1449-1456 (1997).

Lin, et al., "A Porous Silicon-Based Optical Interferometric Biosensor", *Science*, vol. 278, pp. 840-843 (1997).
Magnusson, et al., "New principle for optical filters", *Appl. Phys. Lett.*, vol. 61, No. 9, pp. 1022-1024 (1992).
Magnusson, et al., "Transmission bandpass guided-mode resonance filters", *Applied Optics*, vol. 34, No. 35, pp. 8106-8109 (1995).
Morhard, et al., "Immobilization of antibodies in micropatterns for cell detection by optical diffraction", *Sensors and Actuators* B 70, pp. 232-242 (2000).
Pandey, et al., "Proteomics to study genes and genomes", *Nature* 405(6788):837-46 (2000).
Patel, et al., "Electrically tuned and polarization insensitive Fabry-Perot etalon with a liquid-crystal film", *Appl. Phys. Lett.*, vol. 58, No. 22, pp. 2491-2493 (1991).
Statement of Applicants dated Jun. 10, 2004.
Patel, et al., "Multi-wavelength Tunable Liquid-Crystal Etalon Filter", *IEEE Photonics Technology Letters*, vol. 3, No. 7, pp. 643-644 (1991).
Patterson, S.D., "Proteomics: the industrialization of protein chemistry", *Current Opinions in Biotechnology.* 11(4):413-8 (2000).
Peng, et al., "Experimental demonstration of resonant anomalies in diffraction from two-dimensional gratings", *Optics Letters* vol. 21, No. 8, pp. 549-551 (1996).
Peng, et al., "Resonant scattering from two-dimensional gratings", *J. Opt. Soc. Am. A.*, vol. 13, No. 5, pp. 993-1005 (1996).
Raguin, et al., "Structured Surfaces Mimic Coating Performance", *Laser Focus World*, pp. 113-117 (1997).
Sigal, et al., "A Self-Assembled Monolayer for the Binding and Study of Histidine-Tagged Proteins by Surface Plasmon Resonance", *Analytical Chemistry*, vol. 68, No. 3, pp. 490-497 (1996).
Wang, et al., "Design of waveguide-grating filters with symmetrical line shapes and low sidebands", *Optical Society of America*, vol. 19, No. 12, 919-921 (1994).
Wang, et al., "Guided-mode resonances in planar dielectric-layer diffraction gratings", *J. Opt. Soc. Am.*, vol. 7, No. 8, pp. 1470-1474 (1990).
Wang, et al., "Theory and applications of guided-mode resonance filter", *Applied Optics*, vol. 32, No. 14, pp. 2606-2613 (1993).
International Search Report for foreign counterpart application PCT/US01/50723, Sep. 17, 2002.
International Search Report for foreign counterpart application PCT/US03/01175, Aug. 18, 2003.
Invitation to Pay Additional Fees in foreign counterpart application PCT/US01/50723, Aug. 30, 2002.
Haidner, "Zero-Order Gratings Used as an Artificial Distributed Index Medium", *Optik, Wissenschaftiche Verlag GmbH, Stuttgart*, DE, vol. 89, No. 3, pp. 107-112, 1992.
Peng, et al., "Experimental Demonstration of Resonant Anomalies in Diffraction from two-Dimensional Gratings", *Optics Letters, Optical Society of America*, vol. 21, No. 9, pp. 549-551, 1996.
Wilson, et al., "The Optical Properties 1-19 of 'Moth Eye' Antireflection Surfaces", *Optica ACTA*, vol. 29, No. 7, pp. 993-1009, 1982.
Bagnich, et al., "Tunable Optical Filter", Derwent Publications, English Translation, Abstract Only, Derwent Publications Ltd..
Nellen, et al., "Integrated Optical Input Grating Couplers as Biochemical Sensors", *Sensors and Actuators*, 15 (1988) 285-295.
W. Lukosz and K. Tiefenthaler, "Embossing technique for fabricating integrated optical components in hard inorganic waveguiding materials," *Optics Letters*, vol. 8, pp. 537-539 (1983).
K. Tiefenthaler and W. Lukosz, "Integrated optical switches and gas sensors," *Optics Letters*, vol. 10, pp. 137-139 (1984).
Chabay, "Optical Waveguides," *Analytical Chemistry*, vol. 54, pp. 1071A-1080A (1982).
Sutherland et al., "Optical Detection of Antibody-Antigen Reactions at a Glass-Liquid Interface," *Clin. Chem.*, vol. 30, pp. 1533-1538 (1984).
Ronald T. Holm and Edward D. Palik, "Internal-reflection spectroscopy," *Laser Focus*, vol. 15, pp. 60-65 (Aug. 1979).
N.J. Harrick and George I. Loeb, "Multiple Internal Reflection Fluorescence Spectrometry," *Analytical Chemistry*, vol. 45, pp. 687-691 (1973).

P.K. Tien, "Light Waves in Thin Films and Integrated Optics," *Applied Optics*, vol. 10, pp. 2395-2413 (1971).

Dakss, et. al., "Grating Coupler for Efficient Excitation of Optical Guided Waves in Thin Films," *Applied Physics Letters*, vol. 16, pp. 523-525 (1970).

Sutherland et al., "Immunoassays at a Quartz-Liquid Interface: Theory, Instrumentation and Preliminary Application to the Fluorescent Immunoassay of Human Immunoglobulin G," *Journal of Immunological Methods*, vol. 74, pp. 253-265 (1984).

English translation of CH 670 521 A5.

English translation of CH 669 050 A5.

Anderson, et al., "Proteomics: applications in basic and applied biology", *Current Opinion in Biotechnology*, 2000, 11:408-412.

MacBeath, et al., "Printing Proteins as Microarrays for High-Throughput Function Determination", *Science*, vol. 289, pp. 1760-1763, 2000.

deWildt, et a., "Antibody arrays for high-throughput screening of antibody-antigen interactions", *Nature Biotechnology*, vol. 18, pp. 989-994, 2000.

Cunningham, et al., "A plastic colorimetric resonant optical biosensor for multiparallel detection of label-free biochemical interactions", *Sensors and Actuators B*, 85 (2002) 219-226.

Caruso, et al., "Quartz Crystal Microbalance Study of DNA Immobilization and Hybridization for Nucleic Acid Sensor Development", *Analytical Chemistry*, vol. 69, No. 11, pp. 2043-2049, 1997.

Hefti, et al, "Sensitive detection method of dielectric dispersions in aqueous-based, surface-bound macromolecular structures using microwave spectroscopy", *Applied Physics Letters*, vol. 75, No. 12, pp. 1802-1804, 1999.

Wu, et al., "Bioassay of prostate-specific antigen (*PSA*) using microcantilevers", *Nature Biotechnology*, vol. 19, pp. 856-860, 2001.

Wasserman, et al., "Structure and Reactivity of Alkylsiloxane Monolayers Formed by Reaction of Alkyltrichlorosilanes on Silicon Substrates", *Langmuir*, 5, 1074-1087, 1989.

Kallury, et al., "X-ray Photoelectron Spectroscopy of Silica Surfaces Treated with Polyfunctional Silanes", *Anal. Chem.*, 60, 169-172, 1988.

Cunningham, et al., "Colorimetric resonant reflection as a direct biochemical assay technique", *Sensors and Actuators B*, 81 (2002) 316-328.

Mullaney, et al., "Epitope Mapping of Neutralizing Botulinum Neurotoxin A Antibodies by Phage Display", *Infection and Immunity*, vol. 69, No. 10, pp. 6511-6514, 2001.
Neuschafer et al., Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
U.S. Appl. No. 09/929,957, filed Aug. 15, 2001.
U.S. Appl. No. 09/930,352, filed Aug. 15, 2001.
U.S. Appl. No. 10/415,037, filed Oct. 23, 2001.
U.S. Appl. No. 10/399,940, filed Oct. 23, 2001.
U.S. Appl. No. 10/059,060, filed Jan. 28, 2002.
U.S. Appl. No. 10/201,818, filed Jul. 23, 2002.
U.S. Appl. No. 10/237,641, filed Sep. 9, 2002.
U.S. Appl. No. 10/277,908, filed Aug. 26, 2002.
U.S. Appl. No. 10/233,730, filed Sep. 3, 2002.
U.S. Appl. No. 10/180,374, filed Jun. 26, 2002.
U.S. Appl. No. 10/180,647, filed Jun. 26, 2002.
U.S. Appl. No. 10/253,846, filed Sep. 25, 2002.
U.S. Appl. No. 10/196,058, filed Jul. 15, 2002.
U.S. Appl. No. 10/667,696, filed Sep. 22, 2003.
U.S. Appl. No. 10/058,626, filed Jan. 28, 2002.
Bertoni, et al., "Frequency-Selective Reflection and Transmission by a Periodic Dielectric Layer", *IEEE Transactions on Antennas and Propagation*, vol. 37, No. 1, pp. 78-83 (1989).
Brundrett, et al., "Normal-incidence guided-mode resonant grating filters: design and experimental demonstration", *Optics Letters*, vol. 23, No. 9, pp. 700-702 (1998).
Peng, "Polarization-control Components and Narrow-band Filters Based on Subwavelength Grating Structures" 1996.
Lenau, Torben; *Material, Silicon Nitride*, 1996, 97, 98.
Cerac, Technical publications: *Tantalum Oxide, $Ta_2O_5$ for Optical Coating*, 2000, Cerac, Inc.
Cunningham et al., *Sensors and Actuators* B 85; pp. 219-226 (2002).
Cunningham et al., *Sensors and Actuators* B 81; pp. 316-328 (2002).
Pandey, A. and Mann, M., *Nature*. 405(6788):837-46 (2000).
Patterson, S.D., *Current Opinions in Biotechnology*, 11(4):413-8 (2000).
International Search Report for foreign counterpart application PCT/US03/01175.

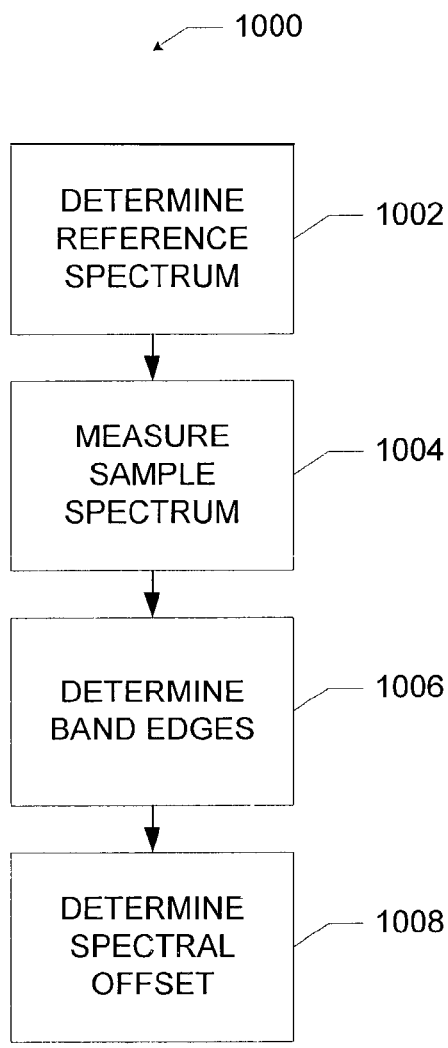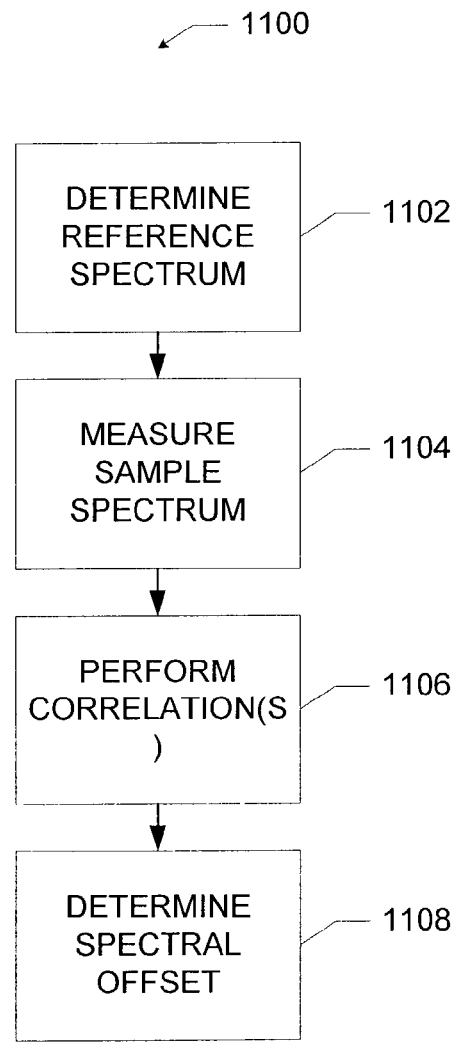
FIGURE 10
FIGURE 11

METHOD AND APPARATUS FOR BIOSENSOR SPECTRAL SHIFT DETECTION

This application is a Continuation-In-Part of U.S. patent application Ser. No. 10/059,060 filed Jan. 28, 2002 now U.S. Pat. No. 7,070,987 and a Continuation-In-Part of U.S. patent application Ser. No. 10/058,626 filed Jan. 28, 2002 now U.S. Pat. No. 6,951,715, both of which are Continuations-in-Part of U.S. patent application Ser. No. 09/930,352, filed Aug. 15, 2001 now U.S. Pat. No. 7,094,595, which claims the benefit of U.S. provisional application 60/244,312 filed Oct. 30, 2000, U.S. provisional application 60/283,314 filed Apr. 12, 2001, and U.S. provisional application 60/303,028 filed Jul. 3, 2001, all of which are hereby incorporated by reference.

BACKGROUND OF THE INVENTION

A. Field of the Invention

The present invention relates to biosensors useful for detecting biological material. More specifically, it is directed to a method and device for determining the amount of shift in an optical biosensor's spectral output.

B. Description of the Related Art

With the completion of the sequencing of the human genome, one of the next grand challenges of molecular biology will be to understand how the many protein targets encoded by DNA interact with other proteins, small molecule pharmaceutical candidates, and a large host of enzymes and inhibitors. See e.g., Pandey & Mann, "Proteomics to study genes and genomes," Nature, 405, p. 837–846, 2000; Leigh Anderson et al., "Proteomics: applications in basic and applied biology," Current Opinion in Biotechnology, 11, p. 408–412, 2000; Patterson, "Proteomics: the industrialization of protein chemistry," Current Opinion in Biotechnology, 11, p. 413–418, 2000; MacBeath & Schreiber, "Printing Proteins as Microarrays for High-Throughput Function Determination," Science, 289, p. 1760–1763, 2000; De Wildt et al., "Antibody arrays for high-throughput screening of antibody-antigen interactions," Nature Biotechnology, 18, p. 989–994, 2000. To this end, tools that have the ability to simultaneously quantify many different biomolecular interactions with high sensitivity will find application in pharmaceutical discovery, proteomics, and diagnostics. Further, for these tools to find widespread use, they must be simple to use, inexpensive to own and operate, and applicable to a wide range of analytes that can include, for example, polynucleotides, peptides, small proteins, antibodies, and even entire cells.

For the majority of assays currently performed for genomics, proteomics, pharmaceutical compound screening, and clinical diagnostic applications, fluorescent or colorimetric chemical labels are commonly attached to the molecules under study so they may be readily visualized. Because attachment of a label substantially increases assay complexity and possibly alters the functionality of molecules through conformational modification or epitope blocking, various label-free biosensor technologies have emerged. Label-free detection phenomenologies include measuring changes in mass, microwave transmission line characteristics, microcantilever deflection, or optical density upon a surface that is activated with a receptor molecule with high affinity for a detected molecule. The widespread commercial acceptance of label-free biosensor technologies has been limited by their ability to provide high detection sensitivity and high detection parallelism in a format that is inexpensive to manufacture and package. For example, biosensors fabricated upon semiconductor or glass wafers in batch photolithography/etch/deposition processes are costly to produce and package if the sensor area is to be large enough to contain large numbers of parallel assays. Similarly, the requirement of making electrical connections to individual biosensors in an array poses difficult challenges in terms of package cost and compatibility with exposure of the sensor to fluids.

Biosensors have been developed to detect a variety of biomolecular complexes including oligonucleotides, antibody-antigen interactions, hormone-receptor interactions, and enzyme-substrate interactions. In general, biosensors consist of two components: a highly specific recognition element and a transducer that converts the molecular recognition event into a quantifiable signal. Signal transduction has been accomplished by many methods, including fluorescence, interferometry (Jenison et al., "Interference-based detection of nucleic acid targets on optically coated silicon," Nature Biotechnology, 19, p. 62–65; Lin et al., "A porous silicon-based optical interferometric biosensor," Science, 278, p. 840–843, (1997)), and gravimetry (A. Cunningham, Bioanalytical Sensors, John Wiley & Sons (1998)).

Of the optically-based transduction methods, direct methods that do not require labeling of analytes with fluorescent compounds are of interest due to the relative assay simplicity and ability to study the interaction of small molecules and proteins that are not readily labeled. Direct optical methods include surface plasmon resonance (SPR) (Jordan & Corn, "Surface Plasmon Resonance Imaging Measurements of Electrostatic Biopolymer Adsorption onto Chemically Modified Gold Surfaces," Anal. Chem., 69:1449–1456 (1997), grating couplers (Morhard et al., "Immobilization of antibodies in micropatterns for cell detection by optical diffraction," Sensors and Actuators B, 70, p. 232–242, 2000), ellipsometry (Jin et al., "A biosensor concept based on imaging ellipsometry for visualization of biomolecular interactions," Analytical Biochemistry, 232, p. 69–72, 1995), evanescent wave devices (Huber et al., "Direct optical immunosensing (sensitivity and selectivity)," Sensors and Actuators B, 6, p. 122–126, 1992), and reflectometry (Brecht & Gauglitz, "Optical probes and transducers," Biosensors and Bioelectronics, 10, p. 923–936, 1995). Theoretically predicted detection limits of these detection methods have been determined and experimentally confirmed to be feasible down to diagnostically relevant concentration ranges. However, to date, these methods have yet to yield commercially available high-throughput instruments that can perform high sensitivity assays without any type of label in a format that is readily compatible with the microtiter plate-based or microarray-based infrastructure that is most often used for high-throughput biomolecular interaction analysis. Therefore, there is a need in the art for compositions, biosensors, methods of preparing biosensors and analytical methods that can achieve these goals.

Guided Mode Resonant Filter Biosensors (GMRFBs) have been shown to be one such biosensor well-suited to determining the degree to which biomolecular interactions are taking place near the sensor surface, without resorting to labeling techniques (including fluorescence, calorimetric, and radiolabeling). GMRFBs also excel at monitoring interactions involving small molecules, proteins, cells, microorganisms, and viruses.

Thus, there exists a need for robust methods of determining the relative shifts of the biosensor spectra. Preferably, such an algorithm can detect spectral changes even when the spectral characteristics of the biosensor do not exhibit a clearly defined peak, or if it has multiple peaks.

SUMMARY OF THE INVENTION

A method and apparatus for performing high-resolution determination of the relative shift of the spectral properties of a biosensor is provided. The shift in the resonance peak of the biosensor is indicative of the amount of material bound to the surface of the biosensor. The apparatus may be used with a colorimetric resonant biosensor having a surface of amine functional groups useful for attaching biological molecules. A preferred biosensor is a Guided Mode Resonant Filter Biosensor (GMRFB).

In one embodiment, parametric fits to the observed resonance peak are used to estimate the exact location of the peak. Peaks thusly obtained over time are subtracted from one another to determine spectral shifts.

In another embodiment, the cross correlation function is used to determine the relative location of the spectrum of the unexposed biosensor with respect to those spectra that are altered (e.g., shifted) by the presence of materials bound to the surface of the biosensor. The original spectral measurements or other biosensor reference data are used to generate digital filter coefficients, which are then used to process the subsequent spectral measurements. The filter thus operates as a correlation-based matched filter that provides a peak output at an offset, the offset indicating the amount of spectral shift between the reference spectrum and the altered spectrum.

Alternative embodiments may include obtaining a number of measurements of the exposed biosensor, filtering each set of altered spectral measurements with the matched filter to obtain a correlation signal, and then averaging the correlation signals. Alternatively, the measurements are first averaged and the averaged signal is then processed with the match-filter. If the measurements are taken over a period of time, then time-based trends of resonance shift may be analyzed. Further, the correlation results may then be analyzed with a peak finding algorithm or curve fitting algorithm to locate the correlation peak indicative of the resonance shift.

Still further embodiments identify the spectral shift of the resonance peak by examining the slope of the magnitude of the spectral response (rate of change of the magnitude with respect to frequency). This may include (i) determining at least two reference frequencies around which the slope of the response has the highest magnitudes (ii) using test data, determining at least two test frequencies around which the slope of the response has the highest magnitudes; and (iii) determining the shift of the peak in response to the at least two reference frequencies and at least two test frequencies.

BRIEF DESCRIPTION OF THE DRAWINGS

The objects, features and advantages of the present invention will be more readily appreciated upon reference to the following disclosure when considered in conjunction with the accompanying drawings, in which:

FIGS. 10, 11, and 12 show methods of determining resonance peak offsets.

DETAILED DESCRIPTION OF THE PREFERRED EMBODIMENT

Figure 1:
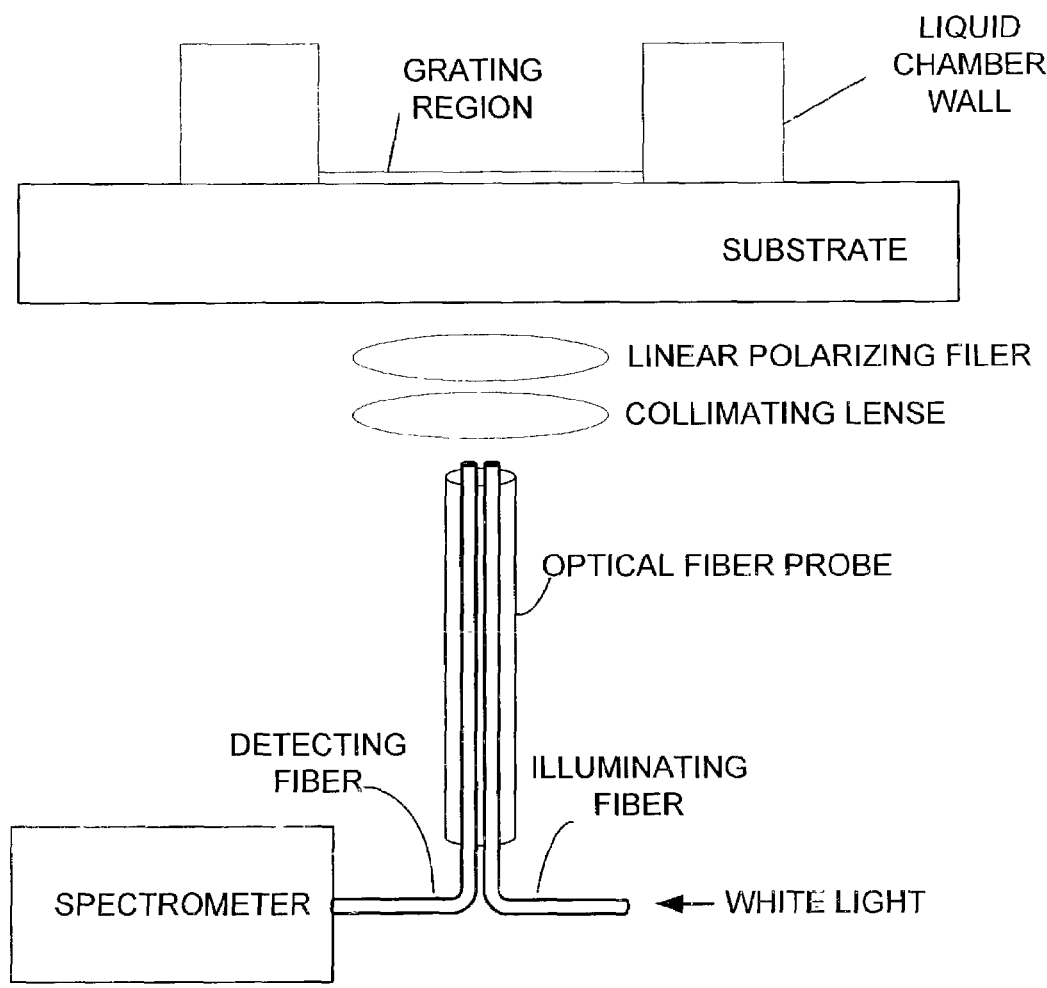
FIG. 1 depicts a preferred embodiment of the instrumentation used to illuminate and read the output of a biosensor.

The preferred calorimetric resonant optical biosensor allows biochemical interactions to be measured on the sensor's surface without the use of fluorescent tags or calorimetric labels. The sensor surface preferably contains an optical structure that, when illuminated with collimated white light, is designed to reflect only a narrow band of wavelengths. The narrow wavelength band is described as a wavelength "peak."

One preferred guided mode resonant filter structure is a one-dimensional linear grating surface structure. The sensor can be manufactured by performing sub-micron definition of grating features using photolithography on the sensor. Alternatively, the sensor can be produced inexpensively over large surface areas using sub-micron microreplication of a master sensor surface structure on continuous sheets of plastic film. Alternative structures, including 2-D or 3-D structures, surface relief structures, glass substrates, discrete plastic film, as well as alternative fabrication methods, may also be used.

The sensor structure can incorporated into standard microtiter plates and used to perform affinity assays based on measuring the biochemical interaction between a substance immobilized on the sensor surface (molecule, peptide, protein, DNA, RNA, phage, cell, bacteria, polymer) and substances within a test sample. The sensor can also be incorporated into other disposable laboratory assay formats, such as microarray slides, flow cells, and cell culture plates. The plastic sensors may be incorporated into the bottoms of bottomless microtiter plates (e.g., microtiter plates having any number of wells, preferably 6, 24, 48, 96, 384, 1536, or 3456 wells), as well as microarrays, and microfluidic devices. These sensor platforms may be used the sensor plate to perform multiple protein-protein binding assays in parallel.

When molecules are attached to the surface of the sensor, the reflected wavelength (color) is shifted due to the change of the optical path of light that is coupled into the grating. By linking receptor molecules to the grating surface, complementary binding molecules can be detected without the use of any kind of fluorescent probe or particle label. The detection technique is capable of resolving changes of ~0.1 nm (nano-meter) thickness of protein binding, and can be performed with the grating surface either immersed in fluid or dried.

The readout system preferably consists of a white light lamp that illuminates a small spot of the grating at normal incidence through a fiber optic probe, and a spectrometer that collects the reflected light through a second fiber, also at normal incidence. Because no physical contact occurs between the excitation, readout system and the grating surface, no special coupling prisms are required and the grating can be easily adapted to any commonly used assay platform, including microtiter plates and microarray slides. A single spectrometer reading is performed in several milliseconds, thus it is possible to quickly measure a large number of molecular interactions taking place in parallel upon a grating surface, and to monitor reaction kinetics in real time. Alternatively, imaging spectrometers can also be used.

It is expected that this system will be most useful in applications where large numbers of biomolecular interactions are measured in parallel, particularly when molecular labels will alter or inhibit the functionality of the molecules under study. High throughput screening of pharmaceutical compound libraries with protein targets, and microarray screening of protein-protein interactions for proteomics are examples of applications that require the sensitivity and throughput afforded by this approach.

A schematic diagram of a preferred system used to illuminate the sensor and to detect the reflected signal is shown in FIG. 1. The sensor depicted in FIG. 1 includes a substrate, a grating surface or region, and liquid chambers to isolate the well. The chamber walls are preferably arranged in a grid pattern to provide isolated regions, or wells, in which reactions may take place. Therefore, each individual well functions as a separate biosensor. A spectrometer, connected to an optical probe head, is used to measure the reflected light. The probe head contains two optical fibers—an illuminating fiber and a detection fiber. In this embodiment, a white light source illuminates a ~1 mm diameter region of the grating surface through a 100 micrometer diameter fiber optic and a collimating lens at nominally normal incidence through the bottom of the microtiter plate. The white light source may be incorporated into the spectrometer, or may be supplied by a separate device.

After passing through the collimating lens, incident light passes through a linear polarizing filter so that the linear grating is excited only with light that is polarized either parallel or perpendicular to the grating lines. Reflected light passes through the polarizing filter again on its way back to the detection fiber. A detection fiber is bundled with the illumination fiber for gathering reflected light for analysis with the spectrometer. One suitable spectrometer for use in the system of FIG. 1 is an HR 2000 High Resolution Spectrometer, which may be obtained from Ocean Optics, at 380 Main Street, Dunedin, Fla., 34698.

In one preferred embodiment, a series of 8 illumination/detection heads are arranged in a linear fashion, so that reflection spectra are gathered from all 8 wells in a 96-well (generally arranged as 8-rows by 12-columns) microtiter plate column at once. The microtiter plate sits upon a motion stage so that each column can be addressed in sequence. The instrument is currently capable of measuring all 96 wells in approximately 15 seconds, limited by the movement rate of the motion stage.

Figure 2:
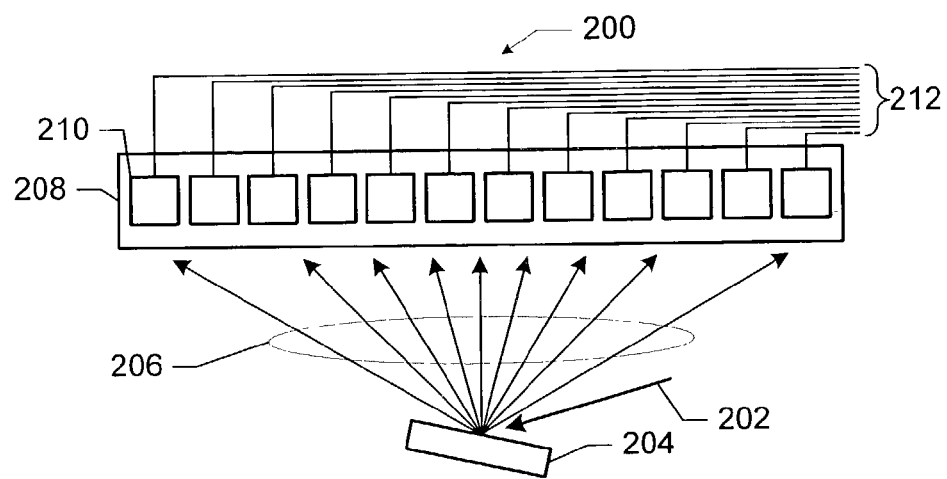
FIG. 2 shows an array of detector devices used to record spectral data.

A spectrophotometer typically measures light intensity at various wavelengths. A block diagram of various components of a spectrophotometer 200 are depicted in FIG. 2. The magnitude of the light may be measured by reflecting the incoming light 202 to be measured off a diffraction grating 204, which acts as a prism. The diffraction grating 204 spreads the received light based on its wavelength, thereby separating it into its constituent components indicated by light rays 206. The spread, or distributed, light is then applied to a sensor 208 made up of a linear array of light sensitive elements or detectors 210 (charge-coupled devices, or CCDs) each of which measures and records the magnitude of the incident light at that CCD element. Typical spectrometers use 2048 CCD elements or pixels. The output 212 from the sensor 208, or CCD array, corresponds to a sampled version of the reflected spectral energy. The output is typically provided over a digital communication link such as an I²C data bus, USB data bus, or equivalent, in the form of a data array.

Numerous factors affect the accuracy of the spectrometer output 212. The grating 204 typically spreads the light approximately one degree per nanometer of wavelength. As can be seen in FIG. 2, the light is not evenly spread onto the linear array. This can be corrected for by curving the linear array of CCDs so that light is distributed more evenly. Alternatively, bins on the outer regions can be made larger to correspond to the same bandwidth. Nevertheless, imperfections in the placement of the CCD sensor array, and imperfections in the size and placement of the CCD elements within the array may affect the accuracy. In addition, imperfections in the grating will result in non-uniform distribution of the light constituents. Still further, quantization errors may be present due to the sampling process.

Each CCD may be considered a wavelength "bin" such that all of the distributed light components which fall onto that CCD element are accumulated and represented as a single value that is output from that CCD element. It can be seen that the width of the CCD element affects the range of wavelengths (frequency bandwidth) that will be incident to it. Ideally, all such bins will have a uniform bandwidth resulting in uniform wavelength quantization. Additionally, the bins are preferably uniformly spaced.

In practice, however, most spectrometers do not have bins with uniform width and spacing. In particular, most spectrometers provide a calibration mechanism to account for any measurable errors so that they may provide the most accurate data output 212 as possible. For example, the above-referenced HR 2000 spectrometer relates the wavelength of a given pixel to a third order function of the pixel number. Calibrated spectrometers typically provide spectral data in output 212 corresponding to non-uniformly spaced wavelength bins. In this case, the data output 212 also includes data values indicating the spacing of the spectral data. In one preferred embodiment, the data 212 includes two data arrays, one array containing spectral magnitude data values, and one array having corresponding bin center wavelengths (or frequencies).

Figure 3:
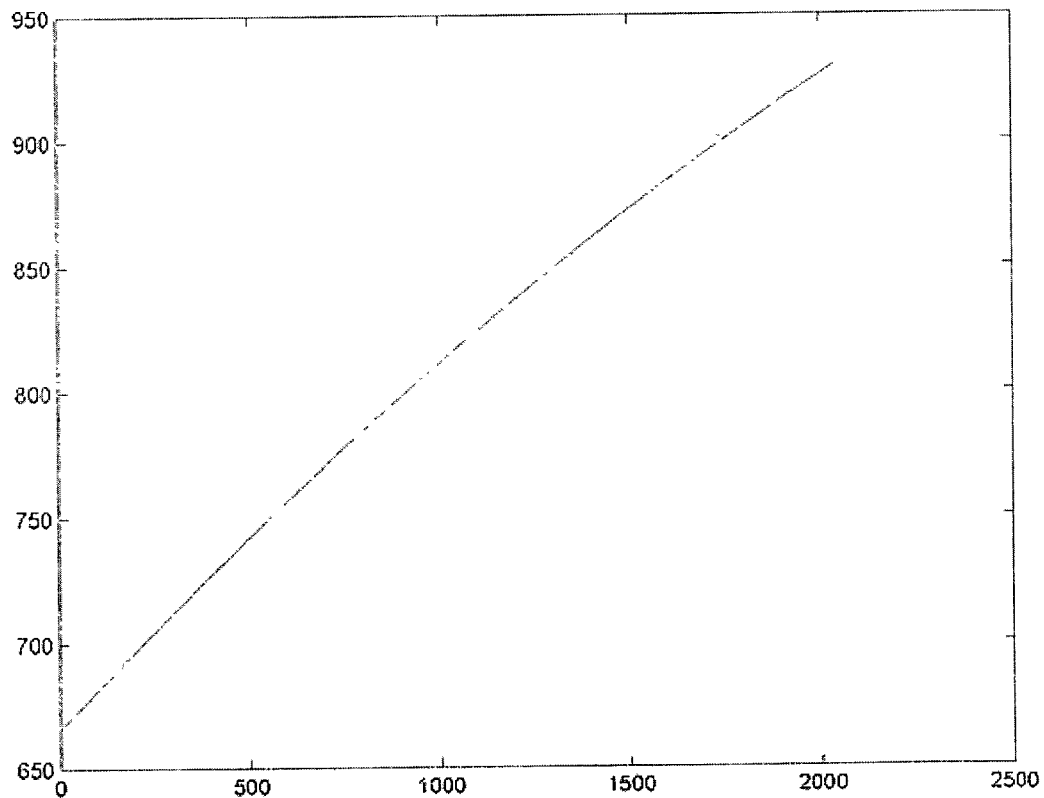
FIG. 3 shows a graph of the relationship between the spectral bin numbers and the spectral wavelengths.
Figure 4:
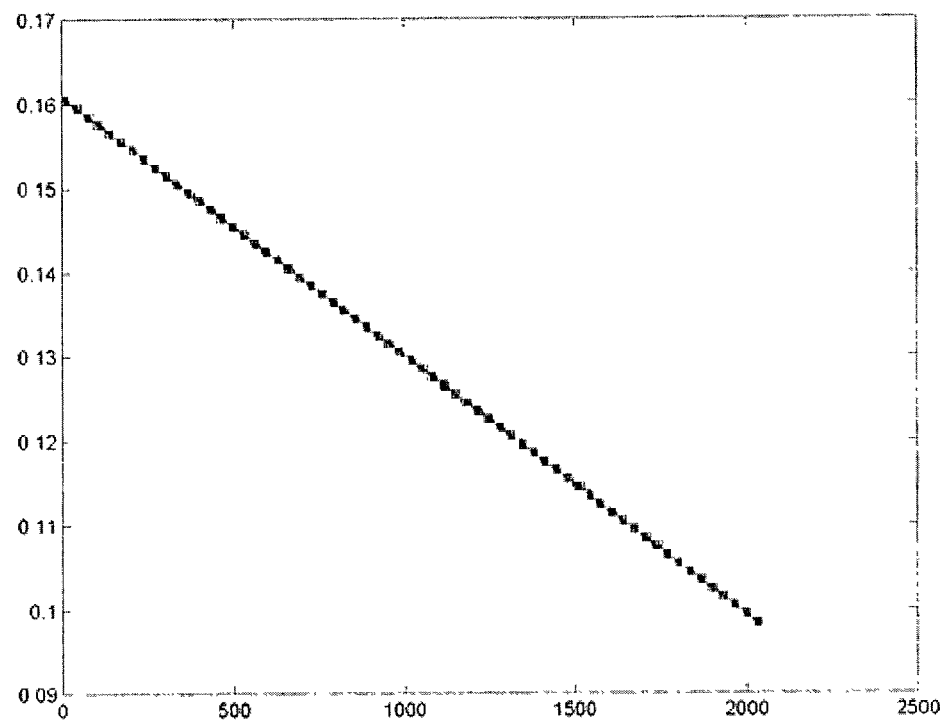
FIG. 4 shows a graph of the relationship between the bin numbers and the spectral width of the bins.
Figure 5:
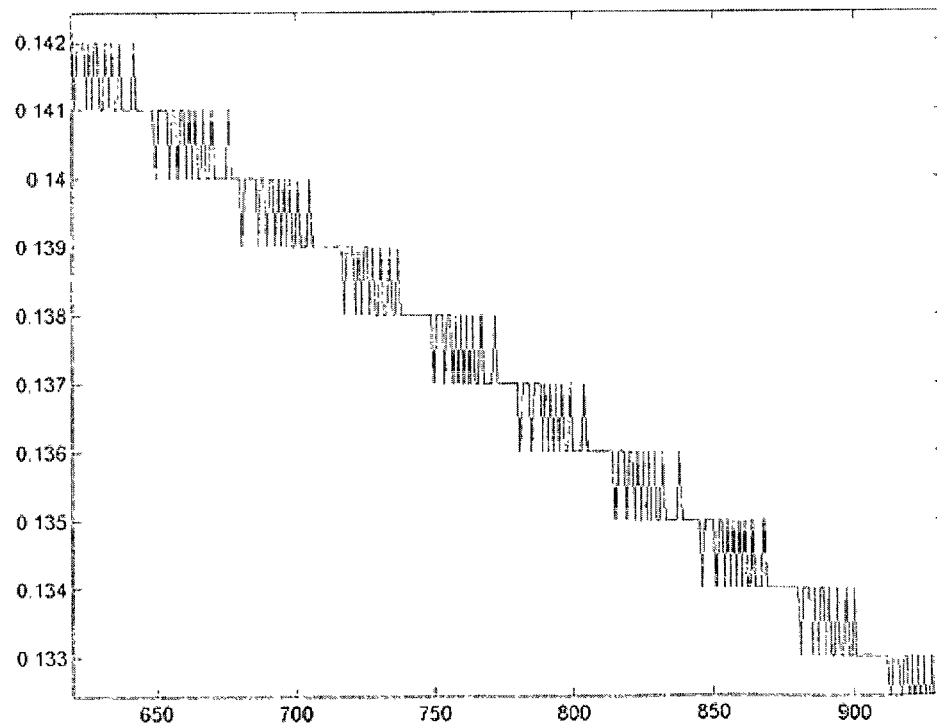
FIG. 5 shows the relationship depicted in FIG. 4 in more detail.

As seen in FIG. 3, the relationship between wavelength and bin number is not linear, indicating the bin width is not uniform. The shape of the curve indicates that higher bin numbers have smaller bin widths. This can be seen more clearly in FIG. 4, which shows the bin width, or resolution, as a function of bin number. Low numbered bins have a width of approximately 0.16 nanometers, while higher numbered bins have a bandwidth of approximately 0.1 nanometers. FIG. 5 shows a smaller region of FIG. 4 (from bin 625 to bin 925), indicating another aspect of the quantization noise. For example, for bins 625 through 650, the bandwidth indicted by the spectrometer oscillates between 0.141 and 0.142 nanometers. This is due to the finite resolution provided by the spectrometer, and results in quantization error.

Spectral Data Interpolation

In some spectral shift detection embodiments, the signal processing used to identify the shift in the peak resonance frequency operates more accurately when the spectral samples are spaced uniformly. Thus, in the event the data 212 from the spectrometer 200 corresponds to non-linearly spaced wavelengths, the data 212 is preferably linearized via an interpolation routine. Numerous interpolation methods can be used, including linear, quadratic, cubic, splines, or digital FIR or IIR filtering of the spectral data points with appropriate zero filling, etc. One preferred interpolation method is piecewise cubic Hermite interpolation. One such piecewise cubic Hermite interpolation routine is found in the Matlab simulation software program, available from The MathWorks, Inc., 3 Apple Hill Drive, Natick, Mass., 01760, as set forth below:

INTERP1 1-D interpolation (table lookup).

YI=INTERP1 (X, Y, XI) interpolates to find YI, the values of the underlying function Y at the points in the vector XI.

The vector X specifies the points at which the data Y is given. If Y is a matrix, then the interpolation is performed for each column of Y and YI will be length (XI)-by-size(Y,2). Out of range values are returned as NaN.

YI=INTERP1 (Y,XI) assumes X=1:N, where N is the length(Y) for vector Y or SIZE(Y,1) for matrix Y.

Interpolation is the same operation as "table lookup". Described in "table lookup" terms, the "table" is [X,Y] and INTERP1 "looks-up" the elements of XI in X, and, based upon their location, returns values YI interpolated within the elements of Y.

YI=INTERP1(X,Y,XI,'method') specifies alternate methods. The default is linear interpolation. Available methods are:
'nearest'—nearest neighbor interpolation
'linear'—linear interpolation
'spline'—cubic spline interpolation
'cubic'—cubic interpolation All the interpolation methods require that X be monotonic. X can be non-uniformly spaced. For faster interpolation when X is equally spaced and monotonic, use the methods '*linear', '*cubic', '*nearest'. For faster linear interpolation when X is non-uniformly spaced see INTERP1Q.

For example, generate a coarse sine curve and interpolate over a finer abscissa:
x=0:10; y=sin(x); xi=0:.25:10;
yi=interp1(x,y,xi); plot(x,y,'o',xi, yi)
See also INTERP1Q, INTERPFT, SPLINE, INTERP2, INTERP3, INTERPN.

Figure 6:
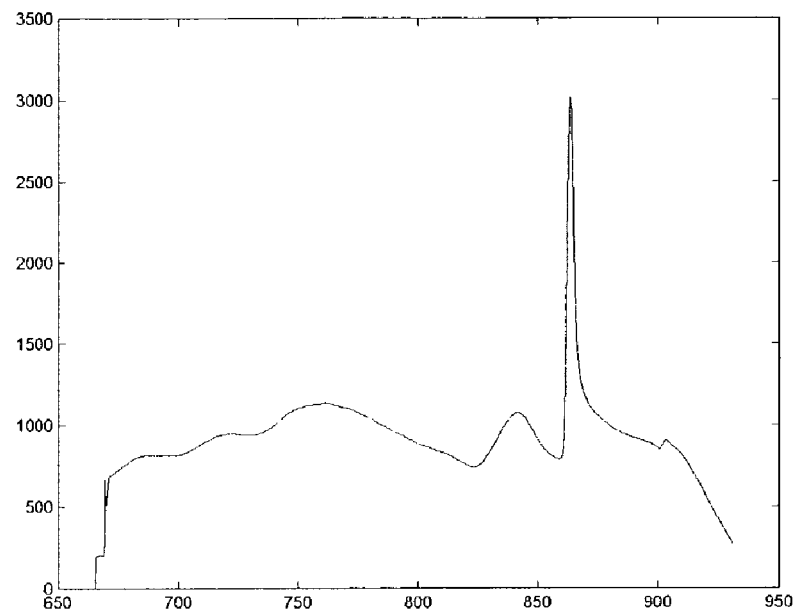
FIG. 6 shows a typical spectral resonance of a biosensor.
Figure 7:
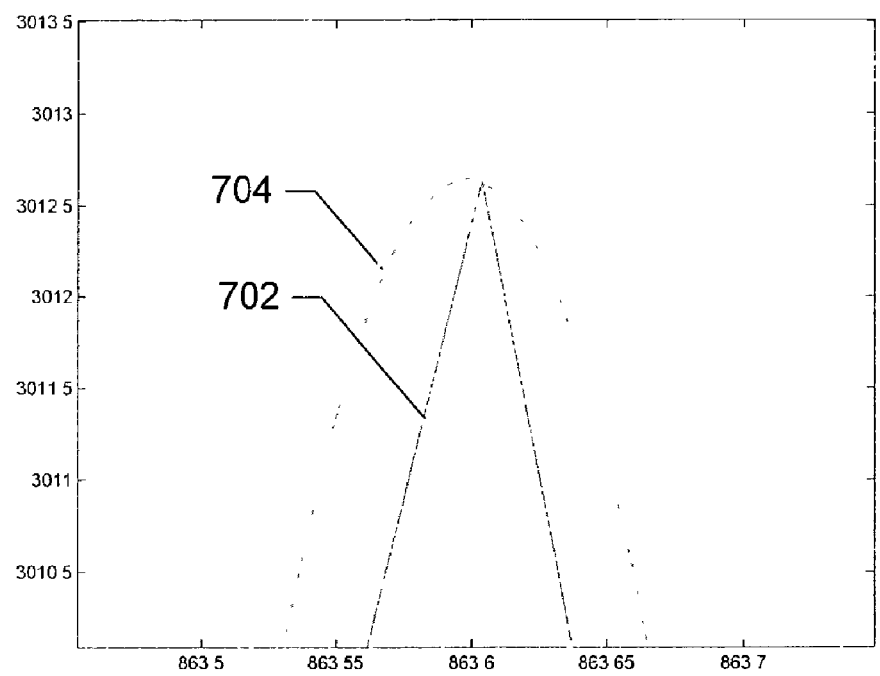
FIG. 7 shows a region of the spectral resonance.

Typically, the preferred interpolation routine operates on the two data vectors (each vector being a one-dimensional array) representing the wavelengths (vector X) and the corresponding spectral magnitudes (vector Y) from the spectrometer. The interpolation routine is also provided with a vector representing the linearly spaced wavelengths (vector XI) for which interpolated spectral magnitude data is desired. The interpolation routine then returns the interpolated values (vector YI) for the spectral magnitudes at the desired wavelengths (given by XI). In one embodiment, a data array of 2048 values may be interpolated into 24,000 values. More or fewer interpolated points may be used. The interpolated data is then processed to determine the wavelength corresponding to the maximum reflected energy, as discussed below. Sample spectra are shown in FIG. 6. FIG. 7, which depicts the data from FIG. 6 between 863.5 to 863.7 nanometers, shows the "raw" data from the spectrometer as curve 702, while the interpolated data is shown in curve 704.

Resonant Peak Determination Using Curve Fitting

In this embodiment, the resonance peaks are determined by fitting curves to the measured spectral data. The curves are then used to determine the peak resonance analytically, preferably using the characteristics of the curves (e.g., locating the point $x_p$ where the curve's derivative is zero, e.g., for the curve $ax^2+bx+c$, where $x_p=-b/2a$).

Typically, a reference curve is determined from data representing the spectral resonance of an unexposed biosensor. The reference curve may be obtained from spectral data representing an average of a number of spectral measurements to decrease the noise inherent in the measured data. The reference may be obtained from the actual biosensor in use, or may be data obtained from a prototypical biosensor and stored in the system for future use.

Then, spectral data is gathered from an exposed biosensor. The curve fitting is separately performed on the spectral data from the exposed biosensor, and the curve characteristics are then used to locate the peak of the shifted spectra. The shift of the peak resonance is then determined by comparing the peak of the reference curve and the peak of the shifted curve obtained from the exposed biosensor.

Preferably the entire set of spectral measurements is not used. The range of data (or "window") used in the curve fitting method may be determined using any suitable criteria, such as a predetermined range of wavelengths on either side of the absolute maximum peak value, or a range of wavelengths based on a multiple (e.g., 1.0, 1.5, etc.) of the half power bandwidth (or any other suitable relative power measurement, such as the one third or one quarter power bandwidth), etc. The user may also select a range of wavelengths by providing input by way of a GUI or command-line prompt. In another preferred embodiment, turning points of the spectrum may be used to identify the relevant spectrum. A turning point is a point where the slope of the spectral response is zero (or a point where the slope is non-monotonic, changing from increasing values to decreasing values, or vice-versa). Preferably the peak is determined and the spectral data surrounding the peak is examined for monotonicity (or alternatively, for zero slope). The spectral data may first be smoothed (e.g., by filtering the data points) prior to identification of the turning points that may be used to define the edges of the resonant peak.

The first analytic curve examined is a second-order polynomial, given by $$y=ax^2+bx+c$$

The least-squares solution to this equation is given by the cost function $$\phi = \sum_{i=1}^{n} (ax_i^2 + bx_i + c - y_i)^2,$$

the minimization of which is imposed by the constraints $$\frac{\partial \phi}{\partial a} = \frac{\partial \phi}{\partial b} = \frac{\partial \phi}{\partial c} = 0.$$

Solving these constraints for a, b, and c yields $$\begin{pmatrix} a \\ b \\ c \end{pmatrix} = \begin{pmatrix} \sum x_i^4 & \sum x_i^3 & \sum x_i^2 \\ \sum x_i^3 & \sum x_i^2 & \sum x_i \\ \sum x^2 & \sum x_i & n \end{pmatrix} \cdot \begin{pmatrix} \sum x_i^2 y_i \\ \sum x_i y_i \\ \sum y_i \end{pmatrix}.$$

An alternative analytic curve that provides better conformance to the data characteristics is the exponential, such as a Gaussian. A simple method for performing a Gaussian-like fit is to assume that the form of the curve is given by $y=e^{ax^2+bx+c}$, in which case the quadratic equations above can be utilized by forming y', where y'=lny. The exponential provides a better fit, providing a 20% improvement over that of the quadratic fit.

Assuming that the exponential curve is the preferred data fitting method, the robustness of the curve fit is examined in two ways: with respect to shifts in the wavelength and with respect to errors in the signal amplitude.

To examine the sensitivity of the analytical peak location to the choice of windows, the window from which the curve fitting is performed is altered to fall 10 sampling intervals to the left or to the right of the true maxima. The resulting shift in mathematically-determined peak location is shown in Table 1. The result is that the peak location is reasonably robust with respect to the particular window chosen: for a shift of ~1.5 nm, the corresponding peak location changed by only <0.06 nm, or 4 parts in one hundred sensitivity.

TABLE 1

Comparison of peak location as a function of window location

| Shift | Window | Peak Location |
|---|---|---|
| Δ = −10 bins | 771.25–782.79 nm | 778.8221 nm |
| Δ = 0 bins | 772.70–784.23 nm | 778.8887 nm |
| Δ = + 10 bins | 774.15–785.65 nm | 7778.9653 nm |

To examine the sensitivity of the peak location with respect to noise in the data, a signal free of noise must be defined, and then incremental amounts of noise added to the signal, while the impact of this noise on the peak location is examined. The ideal signal, for purposes of this experiment, is the average of 10 resonant spectra acquisitions.

Gaussian noise of varying degrees is superimposed on the ideal signal. For each such manufactured noisy signal, the peak location is estimated using the $2^{nd}$-order exponential curve fit. This is repeated 25 times, so that the average, maximum, and minimum peak locations are tabulated. This is repeated for a wide range of noise variances—from a variance of 0 to a variance of 750. The results show that this embodiment of peak detection is extremely robust with respect to random, additive noise. The average peak location, under the range of variances examined, varied by 0. 1 nm about the idealized (i.e., noiseless) solution.

One preferred algorithm for mathematically determining the peak location of a calorimetric resonant biosensor is as follows:

1. Input data $x_i$ and $y_i$, i=1, . . . , n
2. Find maximum
   a. Find k such that $y_k \geq y_i$ for all i≠k
3. Check that maximum is sufficiently high
   a. Compute mean $\bar{y}$ and standard deviation σ of sample
   b. Continue only if $(y_k - \bar{y})/\sigma >$User Threshold
4. Define curve-fit region of 2w+1 bins (w defined by the user)
   a. Extract $x_i$, k−w≦i≦k+w
   b. Extract $y_i$, k−w≦i<k+w
5. Curve fit
   a. $g_i$=ln $y_i$
   b. Perform $2^{nd}$-order polynomial fit to obtain $g_i$ defined on $x_i$, k−w≦i≦k+w
   c. Polynomial fit returns coefficients a, b, c of form $ax^2+bx+c$
   d. Exponentiate: $y'_i = e^{g'_i}$
6. Output
   a. Peak location p given by $x_p = -b/2a$
   b. Peak value given by $y'_p(x_p)$ Resonance Peak Shift Detection Using Correlations An alternative preferred method of determining the resonance peak shift utilizes a correlation process. Using this method, a cross-correlation is performed between a set of reference spectral data and spectral measurements taken from one or more exposed biosensor wells. A correlation filter in the form of an FIR digital filter preferably performs the correlation. As one of ordinary skill in the art will appreciate, the correlation operation may be considered as an FIR digital filtering operation, where the coefficients of the FIR filter are the reverse-ordered sample spectrum values. The output of the filter provides an indication of the amount of shift that has occurred in the biosensor reflectivity due to exposure to a sample under test. Specifically, the peak output of the filter provides an offset parameter that indicates the amount of shift that has occurred in the spectral measurements. The amount of shift is related to the activity of the biosensor, thereby providing a measurement from the biosensor transducer.

The correlation method may provide improved results compared to the curve-fitting methods described above. The correlation method is particularly well suited to new generations of GMRFB biosensors that typically yield much sharper (i.e., narrower) resonance peaks. Specifically, presently available biosensors provide far fewer points with which to perform the curve fitting over the peak region. In addition the resonance spectra may be highly asymmetrical, also making curve fitting less reliable. Finally, the spectra may not exhibit a strong peak under certain conditions, also rendering curve-fitting peak finding algorithms less accurate.

The cross correlation between $f(x)$ and $g(x)$ is defined in the continuous domain by $$f(x) \otimes g(x) = \int_{-\infty}^{\infty} f(\alpha)g(x+\alpha)d\alpha,$$

where α denotes the lag of the correlation. The preferred embodiment is to utilize a normalized cross correlation function, where the integral is normalized by the product of the areas of $ff(x)$ and $g(x)$. In this case, the maximum correlation value is restricted to <=1. For sampled data, the following relationship for the cross correlation $r_{fg}$ of functions $f$ and $g$, is used:

$$r_{fg}(i) = f(n) \otimes g(n) = \sum_j f(j)g(j+i), \qquad \text{(Equation 1)}$$

where i denotes the lag of the correlation, and the summation is over the range of j where the functions are defined, or nonzero. Specifically, the values of g(n) may be the measured spectrum of the exposed biosensor, and the values of $f(n)$ may be the reference spectrum of the biosensor (the samples would be arranged in reverse order if conventional FIR filtering equations are used). As discussed above, the summation may be normalized by, e.g., the sum of all $f$ values and the sum of all g values.

In an alternative embodiment, only a portion of the spectrum may be used in the cross correlation function. Specifically, only the portions near the peak need be included. As seen in FIG. 6, exemplary spectral data are displayed. The most pertinent component of the spectral data is the peak of the response. As shown in FIG. 6, one embodiment may use the range between 800 and 900 nanometers. As with the curve-fitting embodiment, the ranges may be determined using any suitable criteria, such as a predetermined range of wavelengths on either side of the absolute maximum peak value, or a range of wavelengths based on a multiple of the half power bandwidth, turning points, user input, etc.

Figure 8:
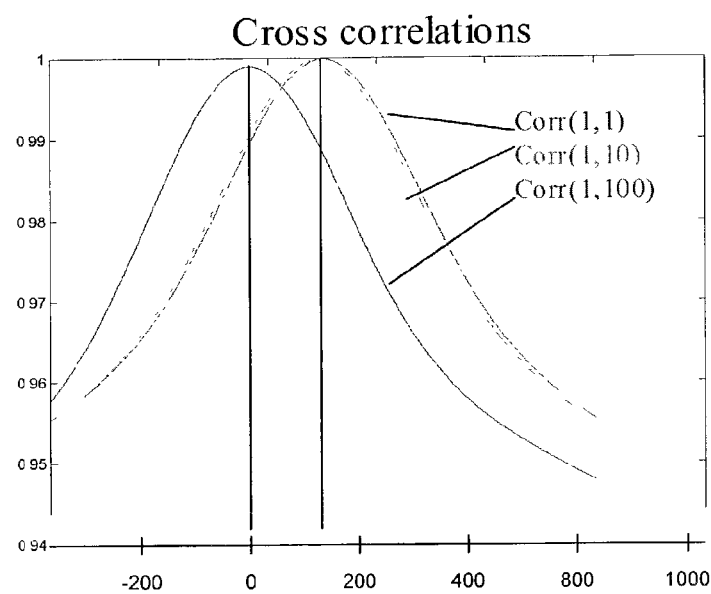
FIG. 8 shows correlation data.

Using the relation given in equation 1, if the reference data is represented by $f(n)$ and the test data is represented by $g(n)$, then $g(n)$ is shifted to the left for positive i, and shifted right for negative i. In this manner, the index i corresponding to the peak output of the filter (the value of i where $r_{fg}=\max(r_{fg}(i))$) indicates the wavelength shift of the spectrum, with positive values indicating an increase in wavelength (decrease in frequency), and negative values indicating a decrease in wavelength (or increase in frequency). Because the wavelengths are linearly spaced, the index may be converted into a change-in-wavelength value by multiplying the index by the sampling interval. A typical correlation output is shown in FIG. 8, having a peak value at an offset (the offset corresponding to a peak correlation value may be referred to as a lag parameter) of approximately 136 samples. In the example of FIG. 8, each sample represents 0.01 nanometers, thus indicating a peak resonance shift of 1.36 nanometers. Thus, the lag parameter may be expressed in terms of samples, or alternatively in terms of wavelength values.

Alternatively, the output of the correlation filter may be interpolated to find a peak offset that may lie between integer multiples of the sampling interval. In this embodiment, the correlator output is provided to an interpolation routine, such as a piecewise cubic Hermite interpolation routine or other suitable routine as discussed previously. After performing cross correlation, the resulting correlation curve is a well-behaved, highly symmetrical function. To fit a curve to the resulting correlation function, numerous analytical functions can be used, including polynomial and exponential curves. One preferred embodiment is to utilize a quadratic curve, since quadratics are fast to compute, and the resulting fit is of high quality.

Reference data is first obtained from the probe to determine the spectral reflectivity of the biosensor prior to exposure of the biosensor to the sample under test. A plurality of measurements may be made and the results averaged to represent the reference spectrum. Additionally, numerous wells may be used for a given test, and the reference data may be calculated for each well, or the data may be averaged over some or all of the wells to obtain a reference spectrum. The reference spectra (or spectrum) are then used as filter coefficients in the correlation filter, (e.g., $f(n)$).

After the biosensor is exposed to the sample under test, the optical probe and spectrometer are used to collect spectral data. The cross correlation can be utilized in a variety of ways. In a sequence of n spectra, where n is large, one can correlate the reference spectrum against all n spectra. The results may then be averaged. If the rate of a reaction conveys useful information, sample data may be taken at specific intervals, or may be time stamped with the time of data collection. The correlation results may then be analyzed, and the resonant frequency shift may then be plotted as a function of time.

In situations where the time aspects of the biosensor measurements are being analyzed, a series of spectral measurements may be made over a period of time to accommodate a temporal analysis of the reaction under study. In some circumstances the spectral characteristics of the biosensor other than the location of the peak resonance may change significantly from measurement to measurement. This makes correlation-based peak finding somewhat less reliable when the measured spectral data are correlated against a single reference spectrum. Alternatively, the measured spectra may be correlated in a daisy-chain fashion, such that each correlation is performed pair-wise. That is, in cases in which the spectral variations or distortions may be severe, a cascade of correlations can be used, where the 1st spectrum is correlated against the 2nd, the 2nd against the 3rd, and so on. Each such correlation thus provides a measurement of an incremental shift for each time period between corresponding measurements. The total shift may be obtained by summing the incremental shift values. The offsets may be plotted and analyzed to determine kinetic trends, characteristics and/or relationships.

Similarly, a mid-point spectrum may be used as a reference spectrum to correlate against all other measured data sets. Again, because the spectral shape may vary from the beginning of the measurements to the final measurement, a middle spectrum (the n/2-th spectrum, or other mid-point spectrum selected from a plurality of measured spectra) can be used as the reference spectrum in the correlation filter because its spectral shape is likely more similar to the beginning and end spectra. In this embodiment, each correlation will provide offset measurements of the corresponding sampled spectra. The offsets may be plotted and analyzed to determine kinetic relationships. The overall spectral shift may be obtained by adding the peak shifts of two correlations: the mid-point spectrum correlated with the beginning spectral measurement (or the negative of the correlation) and the mid-point spectrum correlated with the final spectral measurement.

Correlation results may be further analyzed using the techniques described above to find a correlation peak. After performing cross correlation, the resulting correlation curve is a well-behaved, highly symmetrical function. To fit a curve to the resulting correlation function, numerous analytical functions can be used, including polynomial and exponential curves. One preferred embodiment is to utilize a quadratic curve, since quadratics are fast to compute, and the resulting fit is of high quality. The curve characteristics may then be used to determine the correlation peak.

Resonance Peak Shift Detection Using Resonance Band Edges

Figure 9:
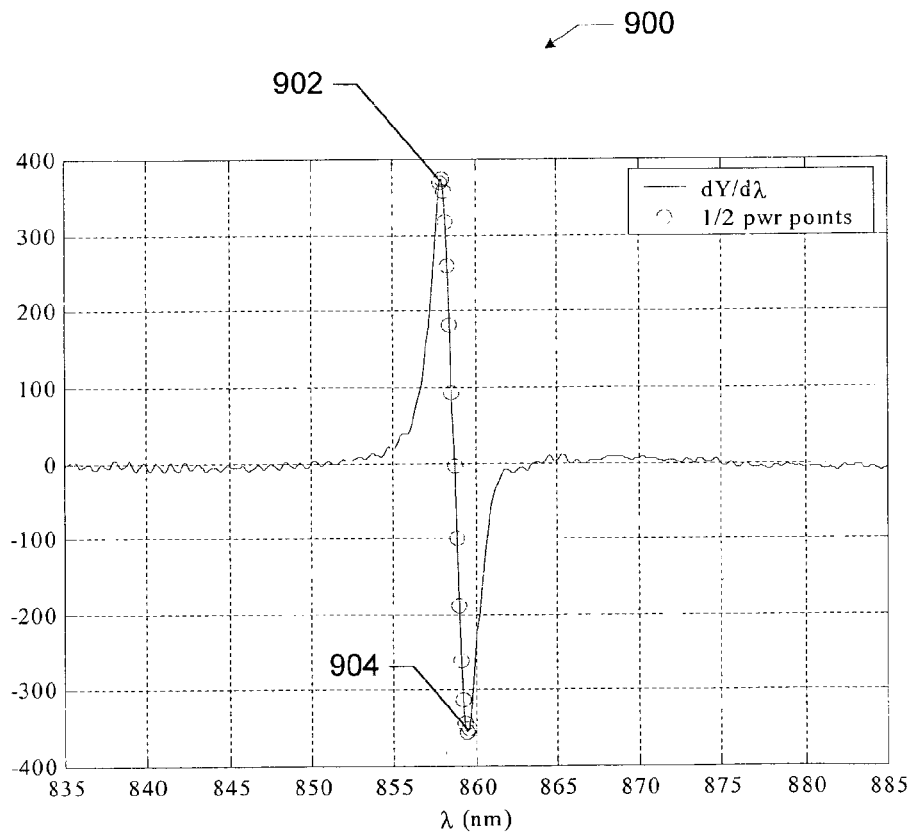
FIG. 9 shows a plot of resonance peak spectra derivative values.

In an alternative embodiment, the shift in resonance wavelength may be determined by analyzing the edges of the peak bandwidth. One technique to determine the edges is simply the 3 dB points (where the power is one half of the peak value). Other power levels may also be used, such as, e.g., the 1.25 dB points (three-quarter power), or the 6 dB points (one-quarter power). Alternative techniques generally include analyzing the derivative of the spectral data waveform. Specifically, the positive and negative peak values of the derivative are indicative of the upper and lower edges of the spectral peak, since these areas exhibit the greatest amount of change per unit wavelength. A plot 900 of typical derivative values is shown in FIG. 9. As can be seen in the Figure, the sample band edges may be determined by first determining an upper maximum 904 and lower maximum 902 of the derivative of the measured sample spectrum, where the upper maximum 904 is the largest negative value of the derivative, and the lower maximum 902 is the largest positive value of the derivative. The sample band edges may then be determined as the wavelengths corresponding to the upper and lower maximum of the derivative of the measured sample spectrum.

Alternatively, the derivative values may be weighted by the signal amplitude. In one embodiment, the derivative values may be divided by the signal amplitude, or by the square of the signal amplitude. In further alternative embodiments, the derivative values may be multiplied by the signal amplitude, or by the square of the signal amplitude. The choice of the scaling factor to use, if any, may be made based on many considerations, including modeling assumptions, and of course, actual performance accuracy based on test data. This technique thus provides a measure of the peak resonance offset based in part on the derivative of the sampled spectra, and the signal amplitude.

Alternatively, the sample band edges may be determined to be the upper and lower wavelengths where the spectrum values are one half the maximum spectral value. As shown in FIG. 9, the points that lie within the half-power bandwidth are very close to the same points that lie between the upper and lower maxima of the derivative.

Once located using one or more of these techniques, the edges of the sampled spectrum may be compared to the reference spectrum. The shift may be determined by averaging the difference between the two lower band edges (one reference, and one sample) and the difference between the two upper band edges (again, one reference, and one sample). Alternatively, the absolute values of the differences may be used. Other techniques of determining spectral shifts using resonance band edges may also be used.

Resonance Peak Shift Detection Using Maximal Likelihood Estimation

An alternative preferred embodiment is to utilize both amplitude and edge information in the determination of a spectral shift. An example of this embodiment can be derived from using a maximum likelihood estimator (MLE). The MLE can incorporate various assumptions, including signal-dependent and signal-independent noise models. A specific implementation utilizing the model that the observed signal $x(\lambda)$ is sampled at different wavelengths $\lambda_i$, in which the observation deviates from the model by an unknown wavelength shift $\theta$ and corrupted by signal dependent noise $w(\lambda)$, this model can be written as:

$$y(\lambda_i)=x(\lambda_i-\theta)+w(\lambda_i).$$

In view of this model, values for $x(\lambda_i)$ may be the reference spectrum obtained from the unexposed biosensor, and values for $y(\lambda_i)$ correspond to the spectral measurements from the exposed biosensor. Additional assumptions, such as the noise $(w(\lambda_i))$ having the property of being characterized by being independently and identically distributed normal distribution with a mean of 0 and a variance of $\sigma_i^2$, or a Poisson distribution with variance $\sigma_i^2$, where $\sigma_i^2$, where $\sigma_i^2=G\ x(\lambda_i-\theta)$ and G represents the gain of the system.

To compute the optimal value for $\theta$, or equivalently to compute the optimal estimation of the amount of shift, under these modeling assumptions, the optimality condition is obtained by setting the derivative of the corresponding cost function to zero, resulting in the following equation:

$$0 = \sum_{i=1}^{N_\lambda} \frac{\left[-\frac{dx(\lambda)}{d\lambda}\Big|_{\lambda=\lambda_i;\theta}\right]}{\sigma_i^2}[y_i - x(\lambda_i - \theta)] \quad \text{(equation 2)}$$

In particular, note that the right-most bracketed term $[y_i-x(\lambda_i-\theta)]$ denotes the error associated with the fit of the model. The error is then weighted by the bracketed term in the numerator, which denotes the slope of the signal, and the term in the denominator, which denotes the signal variance, which empirical observations of the model indicate is proportional to signal amplitude. Specifically, the system gain parameter G relating the signal amplitude to the noise variance may be estimated off-line by taking numerous reference spectrum measurements, and for each wavelength, determining a mean and a variance of the signal measurement. The system measurements, which include the signal of interest plus the noise component, may be modeled as a wavelength-dependent Poisson process $z(\lambda_i)=Gv(\lambda_i)$. where $v(\lambda_i)$ is Poisson. The mean, $m_z(\lambda_i)=Gm_v(\lambda_i))$, is related to the variance, $\sigma_z^2=(\lambda_i)=G^2\ m_v(\lambda_i)$, by the factor G. Thus, G may be obtained by plotting the calculated means versus variances and determining the slope that best fits the graph. Then, because the signal mean is also the value of the reference spectrum $x(\lambda_i)$, the variance of the noise $w(\lambda_i)$ associated with measurements of $y(\lambda_i)$ may be estimated by $\sigma_i^2=Gx(\lambda_i-\theta)$. Note that since Poisson distributions can be approximated by Gaussian distributions when the sample size is large—which is indeed the case in this embodiment of a biosensor, the modeling assumptions in equation 2 remain valid. The gain will vary among systems, and is typically dependent upon the spectrometer, biosensor and other conditions. To solve equation 2, one technique is to linearize equation 2 using a Taylor series expansion. The first two terms of the expansion represent a linearized problem which may then be used to iteratively solve for $\theta$ by computing values of $\Delta\theta^k$ in accordance with:

$$\Delta\theta^k = \underset{\Delta\theta}{\operatorname{argmin}} \left\| \begin{bmatrix} \tilde{y}_1 \\ \vdots \\ \tilde{y}_{N_\lambda} \end{bmatrix} - \begin{bmatrix} -\frac{dx(\lambda)}{d\lambda}\Big|_{\lambda=\lambda_1-\theta_k} \\ \vdots \\ -\frac{dx(\lambda)}{d\lambda}\Big|_{\lambda=\lambda_{N_\lambda}-\theta_k} \end{bmatrix} \Delta\theta \right\|^2_{R^{-1}} \quad \text{(equation 3)}$$

$$\tilde{y}_i = y(\lambda_i) - x(\lambda_i - \theta^k)$$

$$R = diag[\sigma_i^2]$$

Specifically, the values of $y(\lambda_i)$ are the measured spectral data from an exposed biosensor; $x(\lambda_i)$ are the reference spectra; $x(\lambda_i-\theta_\kappa)$ is the reference spectra shifted by an amount equal to an offset estimate at time k, $\theta_\kappa$; and $R^{-1}$ is the inverse of the covariance matrix of the noise. In the formulation defined in Equation 3, as discussed above, the noise at each wavelength is modeled as independent noise, and as such R is a diagonal matrix with the diagonal elements corresponding to the noise in each wavelength channel.

Equation 3 represents a set of linear equations in the form of a standard linear least squares optimization problem. The solution may be obtained using well-known algorithms for the solution of least squares problems. One such solution involves the use of Moore-Penrose pseudo inverse solutions. Other solutions may also be used, such as conjugate gradient, Gaussian elimination, etc., as will be recognized by those of ordinary skill in the art.

One preferred embodiment of the ML estimator is used by solving equation 3 to determine an update $\Delta\theta^{(k)}$ based on equations linearized around $\theta^{(k)}$, using a least squares criterion. The estimate of the spectral offset is then updated by adding $\Delta\theta^{(k)}$ to the previous estimate: $\theta^{(k+1)}=\theta^{(k)}+\Delta\theta^{(k)}$. The accuracy of the estimate of $\theta^{(k)}$ may be enhanced in an iterative manner, by determining a new update based on the revised estimate $\theta^{(k+1)}$. The ML estimator thus provides a measure of the peak resonance offset based in part on the derivative of the reference spectrum, and the reference spectrum and sample spectrum signal amplitudes. Alternatively, the peak resonance offset is based in part on the derivative of the reference spectrum, and measurements or other estimates of the signal-dependent noise.

As will be understood by those of ordinary skill in the art, the ML estimator described above may be modified to accommodate alternative signal models or alternative assumptions. As one example of a modeling variation, one may wish to consider that the reference spectrum as a shifted version of the measured spectrum from the exposed biosensor. In this manner, the roles of the reference spectrum and the measured spectrum are reversed, and the estimation is performed in response to the slope of shifted versions of the measured spectrum, rather than shifted versions of the reference spectrum. Similarly, the estimation of $\sigma_i^2$ may be based on the measured spectrum, resulting in an ML estimator that provides a measure of the peak resonance offset based in part on the derivative of the measured sample spectrum from an exposed biosensor, and the signal amplitude of the measured spectrum. Furthermore, it should be understood that any suitable model may be used to derive alternative ML estimators for use in determining biosensor peak resonance offsets.

Thus, in a preferred embodiment, an iterative ML shift estimation approach is used. Preferably, it operates on data points in the peak region. The peak region contains points of high slope, typically about 30–100 data points. The peak region may be determined using the methods previously described, such as a predetermined range of wavelengths on either side of the absolute maximum peak value, or a range of wavelengths based on a multiple of the half power bandwidth, turning points, user input, etc.

A method 1000 for detecting spectral resonance shifts will now be described with reference to FIG. 10. At step 1002, a reference spectrum is determined. The reference spectrum may be obtained by one or more direct measurements, or a prototypical reference spectrum may be used. This step may include determining reference band edges of the biosensor reference spectrum. At step 1004, the sample spectrum is measured. At step 1006, the band edges of the sample spectrum are obtained. The band edges of the sampled spectrum may be referred to as sample band edges.

The sample band edges may be determined by first determining an upper and lower maximum of the derivative of the measured sample spectrum, where the upper maximum is the largest negative value of the derivative, and the lower maximum is the largest positive value of the derivative The sample band edges may then be determined as the wavelengths corresponding to the upper and lower maximum of the derivative of the measured sample spectrum.

Alternatively, the sample band edges may be determined to be the upper and lower wavelengths where the spectrum values are one half the maximum spectral value. The reference band edges may be referred to as a lower reference band edge and an upper reference band edge, and the sample band edges may be referred to as a lower sample band edge and an upper sample band edge.

As a further alternative, the sample band edges may be determined to be the upper and lower turning points, which are the wavelengths corresponding to the turning points associated with the edges of the resonance peak. Step 1006 may optionally include an interpolation step to provide linearized data samples prior to band edge analysis.

At step 1008 the spectral offset is determined in response to the change in the locations of the band edges of the reference spectrum and the measured spectrum (i.e., the change in the reference band edges and the sampled band edges). The step of determining an offset may include averaging the difference between the lower reference band edge and the lower sample band edge and the difference between an upper lower reference band edge and an upper sample band edge.

An alternative preferred method 1100 for detecting spectral resonance shifts will now be described with reference to FIG. 11. At step 1102, a reference spectrum is determined. The reference spectrum may be obtained by one or more direct measurements, or a prototypical reference may be used. At step 1104, the sample spectrum is measured. At step 1106, the sample spectrum and the reference spectrum are correlated. This may include performing a singles correlation or a plurality of correlations, as discussed above. The choice of the reference spectrum to use in the correlations is also variable among the various embodiments described herein. Further, this step may optionally include an interpolation step to provide linearized data samples prior to correlation. At step 1108 the spectral offset is determined in response to the correlation. This may optionally include curve fitting or interpolation to locate the peak of the correlation output and the corresponding lag parameter.

Figure 12:
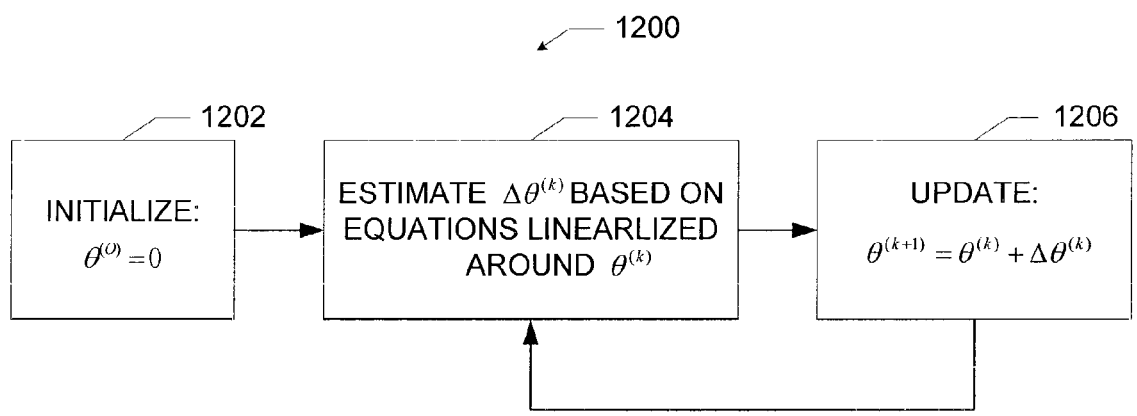

A method 1200 of spectral peak shift detection is depicted in the flow chart of FIG. 12. In this embodiment, the peak shift detection is performed by using the linearized solution (equation 3) defined above, and initializing the beginning offset to zero by setting $\theta^0=0$ at step 1202, then estimating an update $\Delta\theta^{(k)}$ based on equations linearized around $\theta^{(k)}$ at step 1204. Alternatively, the initialization step may be performed by setting $\theta^0$ equal to some other value. Specifically, the initial value may be determined by the peak finding method or the correlation method described above, or according to other criteria, such as anticipated offset values, etc. The estimate of the spectral offset is then updated at step 1206 by determining an offset update value $\Delta\theta^{(k)}$, and adding it to the previous estimate: $\theta^{(k+i)}=\theta^{(k)}+\Delta\theta^{(k)}$. The accuracy of the estimate of $\theta^{(k)}$ may be enhanced by iteratively performing steps 1204 and 1206 until the estimate converges sufficiently. Sufficient convergence may be determined by the magnitude of the calculated value of $\Delta\theta^{(k)}$, i.e., $\Delta\theta^{(k)}$ is below a predetermined threshold.

The peak shifting methods and apparatus described herein are particularly useful in combination with a biosensor having a one, two, or three dimensional grating, typically made of a material having a high refractive index (e.g., zinc sulfide, titanium dioxide, tantalum oxide, and silicon nitride). The grating is preferably formed on a substrate layer (e.g., glass, plastic or epoxy) to support the grating. The grating preferably has a period of about 0.01 microns to about 1 micron and a depth of about 0.01 microns to about 1 micron. The biosensor preferably includes one or more specific binding substances (e.g., nucleic acids, polypeptides, antigens, polyclonal antibodies, monoclonal antibodies, single chain antibodies (scFv), F(ab) fragments, F(ab')$_2$ fragments, Fv Fragments, small organic molecules, cells, viruses, bacteria, and biological samples) are immobilized by e.g., physical adsorption or by chemical binding, on the surface of the grating opposite of the substrate layer. Alternatively, there may be a cover layer (typically a material that has a lower refractive index than zinc sulfide, titanium dioxide, tantalum oxide, and silicon nitride, such as glass, epoxy, and plastic) on the surface of the grating and the binding substances are immobilized on the surface of the cover layer.

In use, the biosensor is illuminated, and a resonant grating effect is produced on the reflected radiation spectrum. Further, the depth and period of the grating are less than the wavelength of the resonant grating effect. The biosensor reflects a narrow band of optical wavelengths when the biosensor is illuminated with a broad band of optical wavelengths. Typically the bandwidth of the resonance peak is in the range of 1–3 nanometers. Such narrow resonance peaks make peak detection (and hence peak offset detection) considerably more difficult than spectra produced from other biosensor structures.

A preferred embodiment of the present invention has been described herein. It is to be understood, of course, that changes and modifications may be made in the embodiments without departing from the true scope of the present invention, as defined by the appended claims. The present embodiments preferably include logic to implement the described methods in software modules as a set of computer executable software instructions. The Computer Processing Unit ("CPU") or microprocessor implements the logic that controls the operation of the system. The microprocessor executes software that can be programmed by those of skill in the art to provide the described functionality.

The software can be represented as a sequence of binary bits maintained on a computer readable medium including magnetic disks, optical disks, and any other volatile or (e.g., Random Access memory ("RAM")) non-volatile firmware (e.g., Read Only Memory ("ROM")) storage system readable by the CPU. The memory locations where data bits are maintained also include physical locations that have particular electrical, magnetic, optical, or organic properties corresponding to the stored data bits. The software instructions are executed as data bits by the CPU with a memory system causing a transformation of the electrical signal representation, and the maintenance of data bits at memory locations in the memory system to thereby reconfigure or otherwise alter the unit's operation. The executable software code may implement, for example, the methods as described above.

It should be understood that the programs, processes, methods and apparatus described herein are not related or limited to any particular type of computer or network apparatus (hardware or software), unless indicated otherwise. Various types of general purpose or specialized computer apparatus may be used with or perform operations in accordance with the teachings described herein. The use of C, C+, C++, Matlab, Mathcad, or other suitable software languages may be used to implement the signaling processing functions and other aspects of the systems described herein. Furthermore, the system may utilize wireless communication systems, and involve portable handheld devices.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

It should be understood that a hardware embodiment might take a variety of different forms. The hardware may be implemented as an integrated circuit with custom gate arrays or an application specific integrated circuit ("ASIC"). Of the course, the embodiment may also be implemented with discrete hardware components and circuitry.

The claims should not be read as limited to the described order of elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

We claim:

1. A method for determining biosensor resonance peak offsets comprising the steps:
    (i) determining a reference spectrum and a sample spectrum, the reference spectrum having a magnitude and a slope; and,
    (ii) determining a peak resonance offset in response to the slope of the reference spectrum.

2. The method of claim 1 wherein the step of determining a peak resonance offset comprises determining an offset that minimizes a criteria for a set of linear equations, wherein each linear ecluation represents the difference between an error term and the product of the slope with a phase shift update, $\Delta\theta$.

3. The method of claim 1 wherein the step of determining a peak resonance offset comprises determining reference band edges in response to the slope of the reference spectrum weighted by the signal amplitudes of the reference spectrum, determining sample band edges in response to the slope of the sample spectrum weighted by the signal amplitudes of the sample spectrum, and determining a relative change in band edges between the reference spectrum and the sample spectrum.

4. The method of claim 1 wherein the step of determining a peak resonance offset is performed by weighting the slope of the reference spectrum by the signal amplitudes of the reference spectrum.

5. The method of claim 1 wherein the roles of the reference spectrum and the sampled spectrum are reversed, and the estimation is performed in response to the slope of shifted versions of the sampled spectrum.

6. The method of claim 1, wherein the step of determining a peak resonance offset in response to the slope of the reference spectrum comprises the steps:
    (a) determining an initial offset estimate;
    (b) determining an offset update value;
    (c) updating the initial offset estimate in response to the offset update value.

7. The method of claim 6 wherein steps (b) and (c) are repeated until a determined offset update value is below a predetermined threshold.

8. The method of claim 6 wherein the step of determining an initial offset value is performed by one of the following steps:
    (a) determining an offset corresponding to a peak resonance value;
    (b) determining an offset corresponding to a peak correlation value;
    (c) determining an offset corresponding to a difference between measured band edges and reference band edges.

9. The method of claim 6 wherein the offset update value is responsive to the derivative of the reference spectrum.

10. The method of claim 6 wherein the offset update value is determined using a least squares criterion.

11. The method of claim 6 wherein the offset update value is determined using a criterion based on maximal likelihood estimation.

12. The method of claim 1 wherein the step of determining a peak resonance offset comprises performing an interative calculation to estimate spectral offset of the sample spectrum based on a maximal likelihood estimation, wherein each iteration is performed in response to the signal amplitude values of the reference spectrum and the sample spectrum and signal slope values of at least one of the reference spectrum and the measured spectrum.

13. The method of claim 12 wherein the iterative calculation is performed until the spectral offset estimate has converged.

14. The method of claim 12 wherein the iterative calculation uses signal values of one of the reference spectrum and the sample spectrum as estimates of noise values.

* * * * *

UNITED STATES PATENT AND TRADEMARK OFFICE
CERTIFICATE OF CORRECTION

PATENT NO. : 7,217,574 B2 Page 1 of 1
APPLICATION NO. : 10/253846
DATED : May 15, 2007
INVENTOR(S) : Pien et al.

It is certified that error appears in the above-identified patent and that said Letters Patent is hereby corrected as shown below:

Col. 2, Line 59, "calorimetric" should read --colorimetric--.

Col. 4, Lines 11, 14, "calorimetric" should read --colorimetric--.

Col. 9, Line 45, "calorimetric" should read --colorimetric--.

Signed and Sealed this

Nineteenth Day of August, 2008

JON W. DUDAS
*Director of the United States Patent and Trademark Office*